United States Patent [19]
Therriault et al.

[11] Patent Number: 5,352,516
[45] Date of Patent: Oct. 4, 1994

[54] WATER-INACTIVATABLE PRESSURE SENSITIVE ADHESIVE

[75] Inventors: Donald J. Therriault, York; Michael J. Zajaczkowski, Yoe, both of Pa.

[73] Assignee: Adhesives Research, Inc., Glen Rock, Pa.

[21] Appl. No.: 828,685

[22] Filed: Jan. 31, 1992

[51] Int. Cl.$^5$ .............................................. C09J 7/02
[52] U.S. Cl. ................................. 428/355; 428/343; 524/339; 524/388; 524/375
[58] Field of Search .............. 428/355, 356, 351, 343; 525/71, 301, 309; 524/323, 401, 339, 388, 375; 526/328, 328.5, 329, 329.3, 329.7, 317

[56] References Cited

U.S. PATENT DOCUMENTS

| | | | |
|---|---|---|---|
| Re. 24,906 | 12/1960 | Ulrich | 526/206 X |
| 3,786,116 | 1/1974 | Milkovich et al. | 525/242 X |
| 4,554,324 | 11/1985 | Husman et al. | |
| 4,656,213 | 4/1987 | Schlademan | 524/533 X |
| 4,693,776 | 9/1987 | Krampe et al. | |
| 4,732,808 | 3/1988 | Krampe et al. | |
| 4,851,278 | 7/1989 | Enanoza | 428/195 |
| 4,871,812 | 10/1989 | Lucast et al. | 428/355 X |
| 4,994,322 | 2/1991 | Delgado et al. | 428/355 X |
| 5,006,582 | 4/1991 | Mancinelli | 525/211 X |
| 5,032,637 | 7/1991 | Therriault et al. | |
| 5,143,972 | 9/1992 | Groves | 525/71 |

*Primary Examiner*—Jenna L. Davis

[57] ABSTRACT

A novel polymeric pressure-sensitive adhesive formulation is provided comprised of a balanced hydrophilic/hydrophobic base polymer compounded with at least one water-soluble tackifying component. Upon contact of the pressure-sensitive adhesive with excess amounts of water, the water-soluble tackifying component is caused to separate from the base polymer, thus decreasing the ability of the base polymer to function as a pressure-sensitive adhesive. The adhesive may subsequently be easily removed from any substrate to which it has been applied.

26 Claims, 1 Drawing Sheet

Figure 1

WATER-INACTIVATABLE PRESSURE SENSITIVE ADHESIVE

BACKGROUND OF THE PRESENT INVENTION

The present invention is directed to water-inactivatable pressure-sensitive adhesives.

It is generally recognized that liquids are effective in reducing the adhesion to skin of pressure-sensitive adhesives, especially in the form as employed in adhesive medical devices. Liquids manifest their effect in several ways such as (1) interaction with the adhesive mass so as to alter the viscoelastic properties of the adhesive resulting in adhesive and/or cohesive failure, or (2) by disrupting the skin/adhesive contact interface. Rarely, although occasionally, the liquid acts upon the interface between the adhesive and any backing support employed. The extent moisture from normal respiration of the skin, and externally-applied liquids such as water.

Those liquids which normally affect the performance of pressure-sensitive adhesive include body exudations, moisture from normal respiration of the skin, and externally-applied liquids such as water.

Coping with the effect of such liquids has been a primary concern of pressure sensitive adhesive suppliers. In general, it is recommended that an application site (such as the skin) be prepared by cleaning and drying immediately prior to application of the adhesive. For most short duration applications, such preparation is quite effective. However, in many situations, the adhesive device is required to remain adhesively secured to the skin for an extended period of time.

To ensure adequate functionality of the adhesive, suppliers have focused upon two avenues of approach. First, hydrophobic adhesives are employed which are substantially incompatible with those liquids with which they will come into contact. Such adhesives are also designed to be fairly aggressive by nature in terms of the degree of adhesion to the skin. Although effective in anchoring the medical device to the skin, the disruption of skin integrity resulting from attempts to remove the device from contact with the skin can be quite painful and/or irritating to the patient. This is particularly true in those areas where repeated applications to the skin are made, or where the skin is fragile. Any disruption to the integrity of the skin which results can be a significant disadvantage in terms of potential infection, as the protective effect of the skin is compromised.

By way of a second approach, liquid is removed from the skin/adhesive interface. This is accomplished by one of two methods. First, the adhesive device is designed so as to provide a water vapor transmission rate through the device which exceeds the normal respiration rate of the skin. This also assists in reducing maceration of the skin commonly experienced with adhesive medical devices. Such adhesive systems are disclosed in U.S. Pat. Nos. 3,645,835; 4,485,809; 4,452,845; and 4,561,435.

Secondly, a "hydroactive" adhesive composition is employed which is water absorbent. This tends to reduce the moisture content at the skin/adhesive interface, while also reducing the frequency of interfacial failure of the adhesive device.

Unfortunately, if the degree of moisture absorbance is excessive, cohesive failure of the adhesive can result. Tacky or sticky adhesive residue will possibly remain on the skin upon removal of the device, which must then be removed from the skin. Examples of such adhesives are disclosed in U.S. Pat. Nos. 3,339,546; 4,147,831; 4,350,785; 4,393,080; 4,505,976; 4,551,490; and 4,650,817.

Polymeric compositions are also known which are comprised of backbone polymers having grafted thereto pendant polymeric moieties. The type of backbone polymer and graft polymeric moiety employed varies depending upon the desired characteristics of the end product. See, for example, U.S. Pat. Nos. 3,786,116; 3,832,423; 3,842,146; 3,862,077; 3,879,494; 3,928,255; 3,989,768; 4,085,168; 4,551,388; 4,554,324; 4,656,213; 4,693,776; 4,732,808; and 4,871,812 which disclose various types of such polymers which may or may not exhibit pressure sensitive adhesive properties.

Typical of the type of polymeric compositions disclosed in the above patents are compositions comprised of a backbone polymer such as an acrylic or methacrylic backbone polymer having attached thereto a graft polymer comprised of a polymerizable macromolecular monomer such as styrene or alpha-methylstyrene. See, for example, U.S. Pat. No 4,554,324, among others, in this regard.

The acrylic pressure sensitive adhesives such as described in U.S. Pat. No. 4,554,324 may be made from an acrylic ester and a polar acrylic monomer. The polar acrylic monomer can be one or a mixture of acrylic acid, acrylamide, acrylonitrile, itaconic acid, etc. The acrylic ester can be any aliphatic ester of acrylic acid. Such monomers are typically polymerized free radically by solution, suspension or emulsion polymerization. The acrylate portion of the copolymer is generally present in a generally high concentration and renders the polymer tacky. The polar monomer increases the ability of the adhesive to bond to a surface.

U.S. Pat. No. 4,693,776 discloses a pressure sensitive skin adhesive composition comprised of a macromet reinforced acrylate copolymer. U.S. Pat. No. 4,871,812 discloses a moldable medical adhesive comprising a blend of an acrylate terpolymer adhesive containing a hydrophilic macromet moiety, and a reinforcing material which is a carbonylamido group containing polymer. U.S. Pat. No. 4,656,213 is directed to an acrylic hot melt pressure sensitive adhesive comprising a polyacrylate graft copolymer which may be compounded with suitable tackifiers and plasticizers to enhance the adhesive properties thereof. U.S. Pat. No. 4,732,808 is directed to a macromer-reinforced pressure sensitive skin adhesive comprised of a macromet reinforced acrylate copolymer.

Said adhesives have been found to suffer from the disadvantage that their adhesive properties are not sufficiently compatible for use with skin (due to inadequate long-term tack), with the result that adhesive failure may occur after a short time due to movement of the skin.

Further, none of the above patents disclose water-inactivatable pressure-sensitive adhesives which may be readily inactivated once applied to the skin and which exhibit highly desirable tack when applied to the skin.

One solution to the noted problems is described in commonly-assigned U.S. Pat. No. 5,032,637 directed to a pressure sensitive adhesive comprised of a hydrophilic base polymer in admixture with a water-soluble tackifying agent. The base polymer comprises at least one polymer of an alkyl vinyl ether: maleic acid ester in admixture with at least one polyvinyl alkyl ether. The tackifying agent may be, for example, ethoxylated alkyl phenols, glycerol, dipropylene glycol and diethylene glycol.

While the adhesive of U.S. Pat. No. 5,032,637 enables many advantages to be achieved, it is still desirable to provide such a composition wherein the adhesive exhibits enhanced stability under conditions of use.

OBJECTS AND SUMMARY OF THE INVENTION

It is thus one object of the present invention to provide a pressure-sensitive adhesive composition which may be easily inactivated so as to enhance the ease of removal of the adhesive from a substrate.

It is also an object of the present invention to provide means to change a permanent pressure-sensitive adhesive to a removable pressure-sensitive adhesive.

It is also an object of the present invention to provide a pressure-sensitive adhesive which exhibits satisfactory skin adhesion properties, while also having the capability of retaining such properties in the presence of minor amounts of moisture.

It is also an object of the present invention to provide a pressure-sensitive adhesive composition which exhibits aggressive adhesive properties but which may be easily removed from a substrate to which it is applied upon application of excess amounts of water thereto.

In accordance with the present invention, there is thus provided a water-inactivatable pressure-sensitive adhesive comprised of a balanced hydrophilic/hydrophobic base polymer in admixture with a water-soluble tackifying agent, said base polymer comprising a phase separated graft copolymer composition comprised of copolymerized monomers A and B to form a backbone polymer having a polymeric moiety grafted thereto, wherein monomer A is a monomeric acrylic or methacrylic acid ester of a non-tertiary alcohol having from 1 to 14 carbon atoms being in the range of about 4 to 12, and monomer B is a polar monomer which is copolymerizable with monomer A.

In accordance with yet another object of the present invention, there is provided, in combination, (1) a water-inactivatable pressure-sensitive adhesive comprised of a balanced hydrophilic/hydrophobic base polymer in admixture with a water-soluble tackifying agent, said base polymer comprising a phase separated graft copolymer composition comprised of copolymerized monomers A and B to form a backbone polymer having a polymeric moiety grafted thereto, wherein monomer A is a monomeric acrylic or methacrylic acid ester of a non-tertiary alcohol having from 1 to 14 carbon atoms being in the range of about 4 to 12, and monomer B is a polar monomer which is copolymerizable with monomer A, and (2) a water-absorbing backing support material to which said adhesive is applied.

In a preferred embodiment, from 1.5 to 2.5 grafts per polymer backbone chain on average are present.

DETAILED DESCRIPTION OF THE INVENTION

The present invention pertains to a water-inactivatable pressure-sensitive adhesive comprised of a balanced hydrophilic/hydrophobic base polymer in admixture with a water-soluble tackifying agent. By way of definition, the pressure-sensitive adhesive is, under normal conditions in its dry state, tacky, viscoelastic and cohesive. The adhesive also exhibits aggressive adhesive properties when applied to skin.

Desirably, upon contact with excess amounts of water the adhesive composition of the present invention undergoes a radical alteration of its viscoelastic properties by means of a controlled phase separation of its constituent components, which renders the composition significantly less tacky. Such alteration involves the migration of the water-soluble tackifier to the adhesive/substrate interface, with the result that the adhesive can be readily removed from contact with the substrate with much less effort than would normally be required.

The base polymer component employed in the pressure-sensitive adhesive composition of the present invention comprises a phase separated graft copolymer composition comprised of copolymerized monomers A and B to form a backbone polymer having a polymeric moiety grafted thereto, wherein monomer A is a monomeric acrylic or methacrylic acid ester of a non-tertiary alcohol having from 1 to 14 carbon atoms, with the average number of carbon atoms being in the range of about 4 to 12, and monomer B is a polar monomer which is copolymerizable with monomer A.

Such compounds have been found to be particularly amenable for use in conjunction with the composition of the present invention, and especially in a pressure-sensitive adhesive used in or in conjunction with medical devices to be applied to the skin of a person. Such base polymer materials are non-toxic and enable a pressure-sensitive adhesive to be formed which is conformable and adherable to a variety of substrates such as a person's skin under a range of conditions.

Exemplary A monomers include but are not limited to esters of acrylic acid or methacrylic acid with non-tertiary alcohols such as 1-butanol, 1-pentanol, 2-pentanol, 3-pentanol, 2-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, 1-dodecanol, etc. Such monomers are known to those skilled in the art.

Exemplary B monomers include but are not limited to one or more of acrylic acid, methacrylic acid, itaconic acid, acrylamide, methylacrylamide, acrylonitrile, methacrylonitrile, diacetone acrylamide, and 2-carboxyl ethyl esters of acrylic acid.

The A monomer will generally be present in the composition in an amount with the range of from about 50 to 80 percent by weight, based on the total weight of the composition, with any additional monomers employed (such as the B monomer) and the polymeric graft moiety comprising the remaining portion of the composition. Further, the graft polymeric moiety will generally comprise from about 2 to 30 percent by weight of the combined amount of the B and C monomers.

Preferably, the polymer graft is a polymeric moiety having a Tg greater than 20° C. and is present in an amount of from 1.5 to 2.5 polymeric moieties per polymer backbone on average, and preferably in an amount of 2 polymeric moieties per chain on average.

The composition of the present invention successfully overcomes certain deficiencies of prior art adhesive compositions by providing for the presence of graft polymeric moieties while also providing for the presence of graft polymer chains in an amount sufficient to provide a reinforcing function which inhibits or restricts flow of the polymer backbone in the presence of the tackifying agent and/or in the presence of water. This assists the adhesive to maintain its integrity upon contact of the composition with water and enhances the ability of the adhesive to be completely removed from the surface to which it is adhered.

The composition of the present invention is characterized as being "phase-separated". That is, the backbone of the copolymer and the attached graft are incompatible and thus do not mix together to form a homogeneous phase. Instead, the copolymer backbone forms a continuous phase within which is dispersed the attached graft phase. The dispersed graft discontinuous phase thus acts to mechanically reinforce the continuous phase.

The polymer graft may be attached to the polymer backbone by conventional techniques such as (1) copolymerization with the respective monomers of the backbone polymer or (2) attachment to a preformed backbone polymer via a suitable functional group subsequent to formation of same by copolymerization of monomers A and B.

With regard to technique (1) which comprises the preferred technique, the adhesive composition of the present invention may be formed from copolymerized monomers A, B and C, wherein (1) monomer A is a monomeric acrylic or methacrylic acid ester of a non-tertiary alcohol, said alcohol having from 1 to 14 carbon atoms with the average number of carbon atoms being in the range of about 4 to 12, (2) monomer B is a polar monomer copolymerizable with said monomer A, the B monomer being present in an amount of up to about 12% by weight of the total weight of all monomers, and (3) monomer C has the general formula X-Z wherein X is a group copolymerizable with said monomers A and B (preferably a vinyl group), and Z is a polymeric graft moiety having a Tg greater than 20° C., said moiety Z being essentially unreactive under copolymerization conditions, wherein said group X of said monomer C and said monomers A and B are copolymerized to form a polymeric backbone chain having pendant therefrom polymeric moiety Z, and wherein said polymeric moiety Z is preferably present in said composition in an amount of from 1.5 to 2.5 polymeric moieties on average per polymeric backbone chain.

A graft polymeric moiety may be prepared as a macromet and copolymerized with one or more A and B monomers which form the backbone polymer such as acrylic acid, acrylamide, methacrylic acid, methacrylamide and alkyl acrylates where the alkyl groups contain from 1 to 14 carbon atoms (e.g., methyl, ethyl, propyl, isopropyl, butyl, amyl, hexyl, 2-ethylhexyl and other octyl, nonyl and decyl acrylates). See, for instance, the disclosure of U.S. Pat. No. 3,786,116, incorporated by reference in its entirety, in this regard.

Typical copolymerization techniques include but are not limited to conventional free radical initiated copolymerization techniques in the presence of a solvent. Suitable copolymerization temperatures range from about 20° C. to 150° C. for periods of time of from 2 to 24 hours until the desired degree of conversion occurs.

Upon completion of the polymerization process, the solvent is removed and a tacky acrylate copolymer results having an acceptable balance of tack and shear adhesive properties at high temperatures.

Depending upon the properties imparted to the backbone polymer as a result of the molecular weight of the particular graft employed, the resulting adhesive may need to be used in solution or emulsion form rather than as a melt adhesive. That is, if the molecular weight of the graft is sufficiently high, the resultant adhesive may be applied to a backing material or substrate in emulsion or solution form, with the water or solvent being removed upon application to the substrate.

With regard to the polymeric graft moiety portion of the adhesive composition, U.S. Pat. Nos. 3,786,116; 3,842,057; 3,842,058; 3,842,059; 3,862,098; 3,862,101, 3,862,102 and 4,554,324 disclose polymerizable macromers which are suitable for use as graft moieties on a backbone polymer as defined.

Preferably, the polymeric moiety Z is formed from a vinyl aromatic monomer such as styrene, alpha-methylstyrene, indene and p-tert-butylstyrene. However, the polymeric moiety Z may also be formed from vinyl toluene, acenaphthalene, acrylonitrile and methacrylonitrile, organic isocyanates including lower alkyl, phenyl, lower alkyl phenyl and halophenyl isocyanates, organic diisocyanates including lower alkylene, phenylene, and tolylene diisocyanates, lower alkyl and allyl acrylates and methacrylates, including methyl, t-butyl acrylates, and methacrylates; lower olefins, such as ethylene, propylene, butylene, isobutylene, pentene, hexene, etc.; vinyl esters of aliphatic carboxylic acids such as vinyl acetate, vinyl propionate, vinyl octoate, vinyl oleate, vinyl stearate, vinyl benzoate, vinyl lower alkyl ethers; conjugated dienes such as isoprene and butadiene, 2-oxazolines such as 2-ethyl-2-oxazoline, and vinyl unsaturated amides such as acrylamide, methylacrylamide, N,N-di (lower alkyl) acrylamides such as N, N-dimethylacrylamide.

The selection of the specific polymerizable monomer for the polymer graft is not critical, since as the above listing suggests, a wide variety of monomers (and the resulting polymeric moieties) can be used with success as a polymeric graft in the claimed composition.

A variety of functional groups may be employed to attach the graft Z to the polymer backbone.

Exemplary functional groups include but are not limited to and —OCH$_2$CH$_2$—O—CHR—CH$_2$, where R is a hydrogen atom or a lower alkyl group.

The molecular weight of the graft polymeric moiety must be sufficient to result in the formation of a "phase-separated" graft copolymer composition. Generally the molecular weight of the graft polymeric moiety will be within the range of from 2,000 to 60,000.

Prior art polymeric compositions are known which are similar in composition to the base polymer of the present invention but which may or may not exhibit pressure sensitive adhesive properties.

For instance, U.S. Pat. No. 4,554,324 discloses acrylate copolymer pressure sensitive adhesive compositions comprised of an acrylic polymer backbone with a polystyrene or poly-alphamethylstyrene polymer grafted thereon.

U.S. Pat. No. 4,554,324 provides that the macromet possess a molecular weight in the range from 2,000 to 30,000. Such molecular weight restrictions are presumably employed to enable the disclosed pressure sensitive adhesive to be melt processed, since the presence of a polymer graft of greater molecular weight would necessitate the need to use more expensive and complicated solution processing techniques.

With regard to the amount of polymer graft present, U.S. Pat. No. 4,554,324 merely teaches that the graft polymer is present within disclosed weight percent ranges. Specifically, the patent states at column 4, lines 30–38 that the moiety C is present in an amount within the range of 1–30% by weight of all monomers present in the composition. The patent further states at column 6, lines 46–54 that the presence of excessive amounts of moiety C in the composition will "over-reinforce" the resultant copolymer, thus decreasing adhesive tack and rendering the composition more "film-like" than "adhesive-like".

U.S. Pat. No. 3,786,116 similarly discloses chemically-joined, phase separated thermoplastic graft copolymers comprised of a backbone polymer having pendent polymer graft moieties. Example 26 of the patent discloses a graft copolymer of poly-alphamethylstyrene terminated with vinyl chloroacetate and butyl acrylate. The poly-alpha-methylstyrene moiety is stated to have a molecular weight of 12,600.

The composition of Example 26 is found to exhibit insufficient plasticity and shear properties to enable the composition to independently serve as a pressure sensitive adhesive.

In contrast to the teachings of the prior art regarding the type and the amount of polymer graft employed in the composition, in a preferred embodiment of the present invention it has been surprisingly found that the use of a polymer graft which is present in an amount of between 1.5 to 2.5 polymeric moieties per polymer backbone on average results in a composition which exhibits high performance properties while desirably retaining desirable adhesive properties.

The presence of the polymer graft on the backbone polymer in the manner stated has been found to result in a composition in which the respective polymeric backbone chains remain bound to one another at temperatures above the Tg of the backbone polymer. That is, the respective separate phases of the backbone polymers and the graft polymeric moieties are caused to be bound together without disadvantageously affecting the adhesive characteristics of the composition.

Further advantages may be attained by employing a graft polymer of sufficient molecular weight to further enhance the performance properties of the adhesive composition.

Molecular weight considerations notwithstanding, it is found that the polymeric network which comprises the adhesive composition can be held together by the presence of from about 1.5 to about 2.5, and preferably about 2, polymeric grafts on average on the backbone polymer. Thus, the phase separated domains present in the composition become interconnected to an extent sufficient to result in an enhanced resistance to flow in the presence of the tackifying agent and/or excessive amounts of water.

Thus, while the prior art such as U.S. Pat. No. 4,554,324 provides for the presence of polymerized graft macromers on an acrylic polymer backbone, the prior art fails to recognize that a critical result to achieve is not the weight percent of macromers present in the composition but is instead the number of chains of the polymeric graft moiety present in the composition (by way of attachment to the polymer backbone).

The distinction between mole percent and weight percent can be dramatic with regard to the amount of graft moiety present in the composition depending upon the molecular weight of the graft. That is, while the presence of from 1.5 to 2.5 grafts per polymer backbone chain on average has been found to enable the objects of the present invention to be attained, the weight percent of graft which is necessary to achieve this result can vary over a wide range depending upon the molecular weight of the graft employed.

The following confirms by way of example the distinction that exists between weight percent and mole percent with regard to the amount of graft present on the backbone polymer of an adhesive composition having a weight average molecular weight of 400,000. For purposes of illustration, the primary monomer is isooctylacrylate with a molecular weight of 184 grams/mole. Again, the goal is to provide an average of 2 grafts per chain, using for purposes of calculation a graft of either an average molecular weight of 50,000 (high molecular weight) or 10,000 (low molecular weight). Each 100 kilogram sample of polymer contains 0.25 moles of polymer. As a result, each 100 kilogram sample of polymer requires the addition of 0.5 moles of graft to yield 2 grafts/polymer chain on average.

0.5 moles of the high molecular weight sample of the graft corresponds to 25 kilograms, while 0.5 moles of the low molecular weight sample of the graft corresponds to 5 kilograms.

The resulting composition thus comprises 25 weight percent of the high molecular weight graft or 5 weight percent of the low molecular weight graft, with 2 graft chains per polymer backbone on average being provided in each instance.

Indeed, the high and low molecular weight grafts would be present in approximately the same mole percentages (i.e., 0.12 and 0.10 mole percent, respectively).

It is thus clear that the reliance of the prior art upon the percent by weight of graft present is alone of little value in determining the number of grafts present on the polymer backbone chain.

In order to demonstrate the advantageous properties of the adhesive compositions of the present invention, various base polymeric adhesive compositions were prepared having the compositions described in the following Examples 1–8:

EXAMPLE 1

A polyacrylate base polymer having a polystyrene graft having a molecular weight of 13,000 is prepared by the following method. In a glass 1 liter reaction vessel the following charge stock was incrementally polymerized under a nitrogen atmosphere at 73° C. over 5½ hours with agitation to a viscosity of 4300 centipoise:

| Isooctyl Acrylate (A monomer) | 134 grams |
|---|---|
| Acrylic Acid (B monomer) | 3 grams |
| Qm-824 (B monomer) | 25 grams |
| Vinyl Acetate (B monomer) | 20 grams |
| Acrylamide (B monomer) | 3.15 grams |
| Diacetone Acrylamide (B monomer) | 3.15 grams |
| Polystyrene Methacrylate Macromer (Graft) | 8.58 grams |
| Benzoyl Peroxide (Initiator) | .62 grams |
| Ethyl Acetate (Solvent) | 367 grams |

Note: Qm-824 is a Rohm & Haas product identified as β-Carboxyethyl Acrylate

EXAMPLE 2

A polyacrylate base polymer having a polystyrene graft having a molecular weight of 20,000 is prepared by the method of Example 1 from the following charge stock:

| Isooctyl Acrylate | 134 grams |
|---|---|
| Acrylic Acid | 3 grams |
| Qm-824 | 25 grams |
| Vinyl Acetate | 20 grams |
| Acrylamide | 3.15 grams |
| Diacetone Acrylamide | 3.15 grams |
| Polystyrene Methacrylate Macromer | 14.39 grams |
| Benzoyl Peroxide | .64 grams |
| Ethyl Acetate | 378 grams |

EXAMPLE 3

A polyacrylate base polymer solution having a viscosity of 2,200 cps and having a polystyrene graft having a molecular weight of 30,000 is prepared by the method of Example 1 from the following charge stock:

| Isooctyl Acrylate | 134 grams |
|---|---|
| Acrylic Acid | 3 grams |
| Qm-824 | 25 grams |
| Vinyl Acetate | 20 grams |
| Acrylamide | 3.15 grams |
| Diacetone Acrylamide | 3.15 grams |
| Polystyrene Methacrylate Macromer | 19.8 grams |
| Benzoyl Peroxide | .65 grams |
| Ethyl Acetate | 388 grams |

EXAMPLE 4

A polyacrylate base polymer solution having a viscosity of 200,000 cp and having a polystyrene graft having a molecular weight of 47,000 is prepared by the method of Example 1 from the following charge stock:

| Isooctyl Acrylate | 134 grams |
|---|---|
| Acrylic Acid | 3 grams |
| Qm-824 | 25 grams |
| Vinyl Acetate | 20 grams |
| Acrylamide | 3.15 grams |
| Diacetone Acrylamide | 3.15 grams |
| Polystyrene Methacrylate Macromer | 30 grams |
| Benzoyl Peroxide | .64 grams |
| Ethyl Acetate | 372 grams |

EXAMPLE 5

A polyacrylate base polymer solution having a viscosity of 4,700 cps after dilution with 150 grams of ethyl acetate and having a polystyrene graft having a molecular weight of 54,000 is prepared by the method of Example 1 from the following charge stock:

| Isooctyl Acrylate | 134 grams |
|---|---|
| Acrylic Acid | 3 grams |
| Qm-824 | 25 grams |
| Vinyl Acetate | 20 grams |
| Acrylamide | 3.15 grams |
| Diacetone Acrylamide | 3.15 grams |
| Polystyrene Methacrylate Macromer | 35.64 grams |
| Benzoyl Peroxide | .62 grams |
| Ethyl Acetate | 368 grams |

EXAMPLE 6

A polyacrylate base polymer solution having a viscosity of 11,600 cps and having a poly-alpha-methylstyrene graft having a molecular weight of 6,600 is prepared by the method of Example 1 from the following charge stock:

| Isooctyl Acrylate | 66.4 grams |
|---|---|
| Acrylic Acid | 1.48 grams |
| Qm-824 | 12.34 grams |
| Vinyl Acetate | 9.87 grams |
| Acrylamide | 1.55 grams |
| Diacetone Acrylamide | 1.55 grams |
| Poly Alpha-Methyl Styrene Macromer | 2.62 grams |
| Benzoyl Peroxide | .31 grams |
| Ethyl Acetate | 181.4 grams |

EXAMPLE 7

A polyacrylate base polymer solution having a viscosity of 18,000 cps and having a poly-alpha-methylstyrene graft having a molecular weight of 12,100 is prepared by the method of Example 1 from the following charge stock:

| Isooctyl Acrylate | 51.1 grams |
|---|---|
| Acrylic Acid | 1.14 grams |
| Qm-824 | 9.5 grams |
| Vinyl Acetate | 7.6 grams |
| Acrylamide | 1.2 grams |
| Diacetone Acrylamide | 1.2 grams |
| Poly Alpha-Methyl Styrene Macromer | 3.26 grams |
| Benzoyl Peroxide | .24 grams |
| Ethyl Acetate | 139.7 grams |

EXAMPLE 8

A polyacrylate base polymer having a viscosity of 1,750 cps and having a poly-alpha-methylstyrene graft having a molecular weight of 30,000 is prepared by the method of Example 1 from the following charge stock:

| Isooctyl Acrylate | 53.8 grams |
|---|---|
| Acrylic Acid | 1.2 grams |
| Qm-824 | 10 grams |
| Vinyl Acetate | 8 grams |
| Acrylamide | 1.26 grams |
| Diacetone Acrylamide | 1.26 grams |
| Poly Alpha-Methyl Styrene Macromer | 7.92 grams |
| Benzoyl Peroxide | .26 grams |
| Ethyl Acetate | 88.6 grams |
| Toluene | 59 grams |

The following Table I demonstrates the effect of the molecular weight of the graft on the performance characteristics of various pressure sensitive adhesive compositions of Examples 1–6 where the graft is present in an amount of two graft chains per polymer backbone chain on average.

TABLE I

EFFECT OF MOLECULAR WEIGHT OF POLYSTYRENE GRAFT

| | Graft Molecular Weight | | | | |
|---|---|---|---|---|---|
| | 13,000 | 20,000 | 30,000 | 47,000 | 54,000 |
| 5 Min Peel (oz) | 86 | 64 | 71 | 50 | 93 |
| 5 lb. Shear (hrs) | >336 | >336 | >336 | >336 | >336 |
| Zoom Shear (min) | 4 | 5 | 15 | 8 | 7 |
| Zoom Shear (Temp,°F.) | 245 | 260 | 500 | 302* | 292** |
| Hot Shear (185° F.) | 10 min | >72 hrs | >72 hrs | >72 hrs | >72 hrs |
| Hot Shear (200° F.) | — | <15 min | >72 hrs | >72 hrs | >72 hrs |
| Hot Shear (250° F.) | — | — | >72 hrs | >72 hrs | >72 hrs |
| Hot Shear (300° F.) | — | — | >72 hrs | — | — |

Note:
5 minute peel: 180 degree peel of the adhesive coated on a polyester backing and bonded to stainless steel.
5 lb. shear: 5 lb. dead load shear test of the adhesive coated on 2 mil. dead soft aluminum and bonded to stainless steel.
Zoom shear: 500 gram dead load shear in which temperature is increased rapidly over time until failure occurs.
Hot shear: 500 gram dead load shear at constant elevated temperature.
*Slippage at 255–265° F.
**Slippage at 269° F.

The data of Table I indicates that the use of a polystyrene graft which is present in an amount of 2 polymeric moieties per polymer backbone chain on average exhibits advantageous cohesive and adhesive strength.

Further, increasing the molecular weight of the polystyrene graft to at least 30,000 enables the resulting pressure sensitive adhesive composition to satisfactorily perform at relatively high temperatures as evidenced by the hot shear tests. That is, a polystyrene graft having a molecular weight of at least 30,000 exhibits satisfactory hot shear strength at temperatures of at least 250° F. By contrast, employing a polystyrene graft having a molecular weight of 13,000 or 20,000 results in a pressure sensitive adhesive which, while otherwise acceptable, exhibits less desirable hot shear values at temperatures as low as 185° and 200° F., respectively.

Table II below summarizes similar tests conducted with adhesive compositions of the present invention of Examples 6–8 including poly-alpha-methylstyrene grafts in an amount of 2 chains per polymer backbone chain on average:

TABLE II

EFFECT OF MOLECULAR WEIGHT OF POLY-ALPHA-METHYLSTYRENE GRAFT

| | Graft Molecular Weight | | |
|---|---|---|---|
| | 6600 | 12,100 | 30,000 |
| 5 Min Peel (oz) | 57 | 54 | 70 |
| 5 lb. Shear (hrs) | 168 | >336 | >336 |
| Zoom Shear (min) | 7 | 15 | 12 |
| Zoom Shear (Temp,°F.) | 290 | 444* | 379 |
| Hot Shear (185° F.) | >72 hrs | >72 hrs | >72 hrs |
| Hot Shear (200° F.) | >72 hrs | >72 hrs | >72 hrs |
| Hot Shear (250° F.) | >72 hrs | >72 hrs | >72 hrs |
| Hot Shear (300° F.) | ** | >72 hrs | >72 hrs |

Note:
5 minute peel: 180 degree peel of the adhesive coated on a polyester backing and bonded to stainless steel.
5 lb. shear: 5 lb. dead load shear test of the adhesive coated on 2 mil. dead soft aluminum and bonded to stainless steel.
Zoom shear: 500 gram dead load shear in which temperature is increased rapidly over time until failure occurs.
Hot shear: 500 gram dead load shear at constant elevated temperature.
*Slippage at 312° F.
**Failure at 290° F.

In contrast to the polystyrene graft, the poly-alphamethylstyrene graft enables the pressure sensitive adhesive to exhibit high temperature stability at relatively low molecular weights. However, particularly advantageous results are achieved at molecular weights of at least 12,000.

In order to demonstrate the advantages provided by the presence of 1.5 to 2.5 graft chains on average to be present on the polymer backbone chain, the following tests were conducted and the results summarized in Table III.

Comparative Examples A and B are exemplary pressure sensitive adhesive compositions whose polymer chains on average contain either 1 polystyrene graft per acrylate polymer backbone chain on average (Comparative Example A) or 3 polystyrene grafts per acrylate polymer backbone chain on average (Comparative Example B).

The undergrafted (Comparative Example A) and overgrafted (Comparative Example B) samples were prepared from the following charge stocks:

| | Comparative Example A | Comparative Example B |
|---|---|---|
| Isooctyl Acrylate | 134 grams | 134 grams |
| Acrylic Acid | 3 | 3 |
| Qm-824 | 25 | 25 |
| Vinyl Acetate | 20 | 20 |
| Acrylamide | 3.15 | 3.15 |
| Diacetone Acrylamide | 3.15 | 3.15 |
| Polystyrene Methacrylate macromer (MW = 13,000) | 4.58 | 13.0 |

The compositions of Example 1 and Comparative Examples A and B were evaluated for adhesive performance, with the results of such evaluations being summarized in Table III below:

TABLE III

EFFECT OF NUMBER OF GRAFT CHAINS ON POLYMER BACKBONE

| | Invention Example 1 | Comparative Example A | Comparative Example B |
|---|---|---|---|
| 5 Min Peel (oz) | 86 | 81 | 73 |
| 5 lb. Shear (hr) | >336 | 48 | 72 |
| Plasticity | 3.38 | 2.77 | 4.16 |
| Grafts/Backbone Chain on Average | 2 | 1 | 3 |

The 5 lb. shear data of Table III demonstrates that a polymer composition having either 1 graft per polymer chain on average (Comparative Example A) or 3 grafts per polymer chain on average (Comparative Example B) exhibits decreased adhesive properties in comparison to the composition of Sample 1 which contains two grafts per polymer chain on average.

Table III demonstrates the dramatic change that occurs when two grafts per polymer chain on average are present on the polymer backbone in comparison to those instances where either 1 or 3 grafts on average are present.

In essence, the pressure sensitive adhesive compositions of Comparative Samples A and B which exhibit adhesive properties on a relatively "short term" or "transient" basis (<72 hours) under the test conditions employed are transformed to a pressure sensitive adhesive composition which exhibits long term or more permanent adhesive properties (>336 hours) merely by modifying the number of grafts on the polymer backbone chain.

The following Table IV confirms that the base polymer composition of the present invention in its preferred embodiments may be formed by blending a plurality of backbone polymer compositions together having a graft copolymer present in an amount outside of the range of 1.5 to 2.5 polymeric moieties per backbone polymer on average whereby the resulting blend contains from 1.5 to 2.5 polymeric moieties per backbone chain on average.

Examples 9, 10 and 11 were prepared comprising pressure sensitive adhesive compositions of differing weight ratio blends of the compositions of Comparative Examples A and B using the weight ratios of 25:75, 50:50 and 75:25, respectively, to yield compositions having 1.5, 2.0 and 2.5 grafts per polymer backbone on average, respectively.

TABLE IV

EFFECT OF NUMBER OF GRAFT CHAINS ON POLYMER BACKBONE BLEND COMPOSITIONS

|  | Invention Example 9 | Invention Example 10 | Invention Example 11 |
|---|---|---|---|
| 5 Min. Peel (oz) | 74 | 70 | 76 |
| 5 Lb. Shear (hr) | >336 | >336 | >336 |
| Plasticity | 2.84 | 3.75 | 4.01 |
| Grafts/Backbone Chain on Average | 1.5 | 2.0 | 2.5 |

The results of Table IV are confirmed by further experimentation wherein an acrylic tackifier graft polymer is admixed with an adhesive composition having one graft per backbone chain on average. The admixture of the two results in a polymer composition having on average 2 grafts per backbone chain. While the tackifier and the adhesive each separately exhibit inadequate shear strength (<2 and <8 hours, respectively) the resultant blend exhibits a highly satisfactory shear strength value of >336 hours.

It should be apparent from the above discussion that the base polymer of the present invention may be formed by the preparation of a phase separated acrylic graft copolymer having the requisite number of grafts per polymer chain or, alternatively, by the physical blending of multiple phase-separated acrylic graft copolymer compositions to yield a blend which contains on average the desired number of grafts per polymer backbone.

The base polymer is advantageously substantially water-insoluble under those conditions normally encountered during use of the adhesive (i.e., under ambient conditions).

The tackifying component of the adhesive compound of the present invention comprises a water-soluble compound of relatively low molecular weight which, when admixed with the base polymer component, serves to tackify the base polymer, with a pressure-sensitive adhesive composition resulting. The tackifier, when used in a pressure-sensitive adhesive to be applied to the skin of a person, is desirably medically non-irritating. The tackifier must also be compatible with the base polymer to permit the tackifier to be homogeneously dispersed therein.

Tackifying components suitable for use in the present invention include, but are not limited to, ethoxylated alkyl phenols and similar amphipathic compounds (i.e., compounds having both hydrophilic and lipophile regions). Water-soluble glycols such as polysorbitol, glycerol, polypropylene glycol and polyethylene glycol (e.g., dipropylene and diethylene glycols) are also suitable for use in the present invention as the tackifying component.

Preferably, the molecular weight of the tackifying component is in the range of from about 50 to 20,000.

Exemplary tackifier components are available from GAF Corporation under the trade name Igepal (a class of various ethoxylated alkyl phenols). Mixtures thereof with polyethylene glycols are also suitable for use in the present invention.

Preferably, the tackifier component and base polymer component are combined in weight ratios ranging from about 0.05:1 to about 1.5:1, and more preferably ranging from about 0.25:1 to about 0.75:1, respectively.

The degree of tack imparted by the tackifying agent depends upon the amount of tackifying agent present, the amount of the polar component present in the polymer backbone, and the solubilizing effect of the tackifying agent.

Once formed, the generally aggressive adhesive properties of the pressure-sensitive adhesive of the present invention may be modified and/or controlled as follows.

Upon contact of the adhesive with an excess or saturating amount of water, water is drawn into the adhesive due to the balanced hydrophilic/hydrophobic character of the base polymer. Catastrophic phase separation of the tackifier from the base polymer is then observed as evidenced by a gross change in the viscoelastic properties of the adhesive. The adhesive is also weakened as water begins to act as a plasticizer. As the water-soluble tackifier component migrates to the substrate/adhesive interface, the original homogeneous nature of the pressure-sensitive adhesive composition is destroyed and the adhesive eventually becomes relatively tackless in comparison to the tack originally exhibited by the adhesive. As liberated tackifier migrates to the adhesive/substrate interface, the dislodgement of the adhesive from the substrate rapidly occurs. Such a sequence of events has been observed to occur relatively rapidly (such as over a period of time of two minutes or so).

The tack exhibited by the water-soluble tackifier alone (upon migration to the interface between the composition and the substrate) is significantly less than that originally exhibited by the pressure-sensitive adhesive. Such reduced tack, together with the phase separation of the original adhesive composition, enables the composition to be easily removed from the substrate. The net effect is that the adhesion exhibited by the saturated adhesive is, after several minutes of being saturated with moisture, about 75–80 percent less than the adhesion originally exhibited. Once the adhesive is removed, only minor amounts of water-soluble tackifier remain on the substrate, which can be easily removed.

Additional conventional pressure-sensitive adhesive modifiers may also be present such as extenders, stabilizers, antioxidants, pigments and fillers. Such modifiers are employed in amounts generally deemed to be conventional to those skilled in the art.

The water-inactivatable pressure-sensitive adhesive composition of the present invention is normally employed in conjunction with a porous supporting backing material having the ability to (1) absorb excess or saturating amounts of moisture and (2) provide structural integrity for the adhesive. Such water-absorbent backing materials include but are not limited to woven and non-woven fabrics comprised of natural or synthetic materials. For instance, materials such as cellulose acetate tricots can be employed with success. Additional types of backing materials which can be employed include knitted fabrics, such as knitted nylon, elastic fabrics or bandages, foams, etc. A suitable exemplary synthetic fiber non-woven backing layer is available from DuPont under the designation "Sontara".

The major requirement with regard to the type of absorbent backing materials employed is that the material have the capability to absorb excess or saturating amounts of moisture, with such amounts being on the order of about 25 percent or more based on the weight of the adhesive.

It is also desirable for the backing support material to be one to which the pressure-sensitive adhesive can be well bonded and/or anchored. Such bonding or anchoring ensures that, upon contact of excess amounts of moisture with the adhesive, any delamination or phase separation which occurs will occur at the interface between the adhesive layer and the substrate, instead of between the adhesive layer and the backing material.

The pressure-sensitive adhesive can be coated upon the backing material by conventional means and the adhesive dried to yield a tacky pressure-sensitive adhesive supported on the material.

It is further advantageous for the pressure-sensitive adhesive composition of the present invention to exhibit significant water vapor transmission rates to enable the adhesive to satisfactorily function in the presence of moisture in those amounts normally encountered under ambient conditions of use (such as while in contact with the skin of a person).

It has been determined that the adhesive compositions of the present invention exhibit water vapor transmission rates on the order of at least 1000 g/M$^2$/day. Such a water vapor transmission rate is of such magnitude that the adhesive of the present invention can be employed without much regard for the thickness of the adhesive layer. That is, the adhesive composition of the present invention can be employed on a backing material in a layer having a thickness on the order of 0.5 to 3.5 mils without fear of significantly inhibiting the water vapor transmission rate of the adhesive.

The pressure-sensitive adhesive compositions of the present invention can absorb significant amounts of moisture without adversely affecting tack properties. For example, it has been determined that up to about 20 to 25 percent by weight of moisture (based on the weight of the adhesive layer) can be absorbed without catastrophic loss of probe tack, with absorbed amounts in excess of about 25 percent by weight of moisture beginning to adversely affect probe tack.

The absorption of moisture in amounts in excess of about 30 percent by weight will generally result in catastrophic loss of tack, resulting in ease of removal of the adhesive layer from the substrate in a manner consistent with the objects of the present invention. As a result, the adhesive composition is particularly amenable for use in connection with medical devices which are adhesively-applied in the neonatal and geriatric areas. Such adhesives can be employed, for example, in adhesive tapes, bandages, surgical drapes, etc.

EXAMPLE 9

A water-inactivatable pressure-sensitive adhesive composition of the present invention was prepared as follows.

200 grams of the base polymer of Example 1 in the form of a viscous fluid was admixed with stirring 30 grams of Polysorbate 80 tackifier to achieve a homogeneous admixture. Polysorbate 80 is commercially available from ICI Americas, Inc. and comprises polyoxyethylene (20) sorbitan oleate.

To test the moisture capacity and the effect thereof on the adhesive properties of the thus-formed pressure-sensitive adhesive of the present invention, adhesive samples made in accordance with the present invention were cast onto a siliconized release liner, dried, and transferred to a 2 mil thick PET film.

The thus-formed pressure-sensitive adhesive having a PET backing layer was found to exhibit the following properties: probe tack of 540 grams, 180 peel of 1.13#/in, and 500 g deadload shear of 17.8 minutes.

Figure 1:
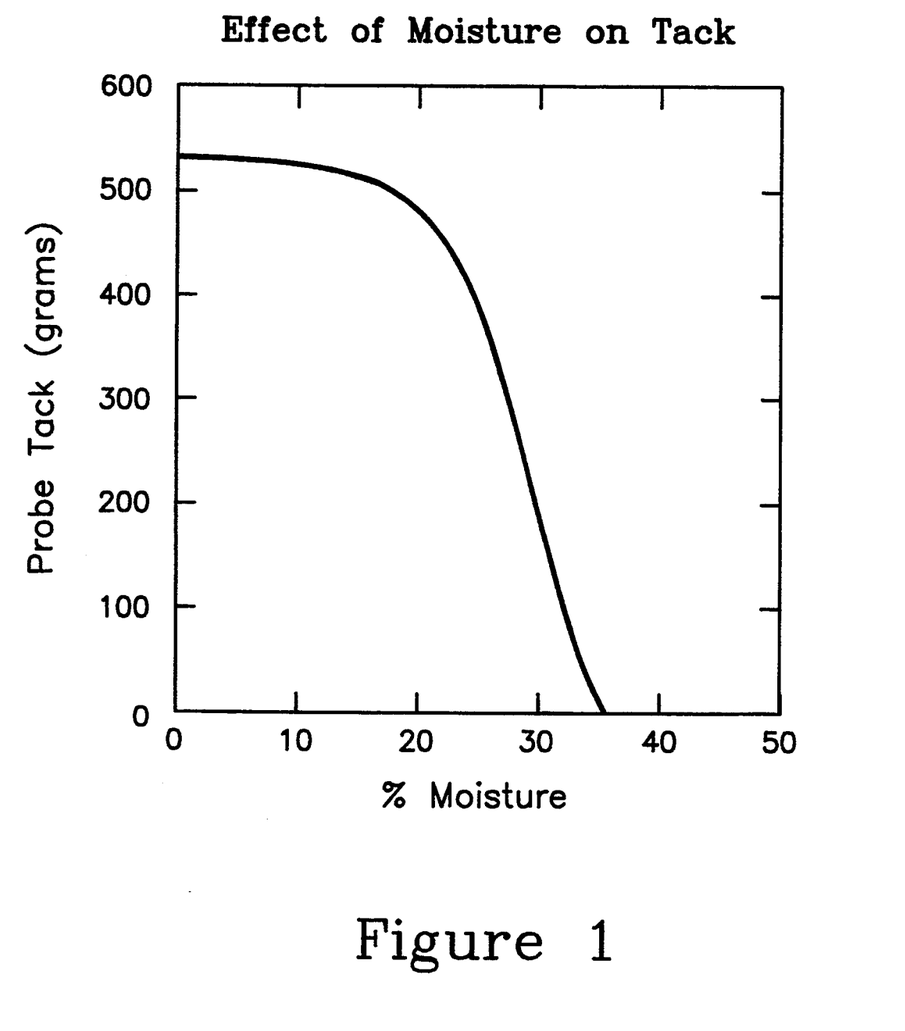
FIG. 1 depicts the relationship between the tack exhibited by the pressure-sensitive adhesive of the present invention and the amount of moisture absorbed by the adhesive.

Samples of the adhesive laminate were then placed on Payne cups loaded with water, and conditioned at various temperatures. At prescribed time intervals, samples were removed and tested for Probe Tack (tack measured as grams force) and moisture content (% moisture based on adhesive weight). The results are depicted in FIG. 1.

From the figure, it is demonstrated that the water-inactivatable adhesive of the present invention can absorb up to about 20 to 25% of its own weight without catastrophic loss of Probe Tack. At absorption values of between 25 and 30%, a change in the viscoelastic properties of the adhesive can be observed. Accordingly, an amount of water in excess of about 30% based on the weight of the adhesive is found to reduce the Probe Tack to substantially negligible values, thus inactivating the adhesive.

What is claimed is:

1. A water-inactivatable pressure sensitive adhesive comprised of a hydrophilic/hydrophobic base polymer component in admixture with a water-soluble tackifying agent for said base polymer, said base polymer component comprising a phase separated graft copolymer composition comprised of copolymerized monomers A and B to form a backbone polymer having a polymeric moiety grafted thereto, wherein monomer A is a monomeric acrylic or methacrylic acid ester of a non-tertiary alcohol having from 1 to 14 carbon atoms, with the average number of carbon atoms being in the range of about 4 to 12, and monomer B is a polar monomer which is copolymerizable with monomer A, wherein said graft polymeric moiety is present in an amount of from about 1.5 to 2.5 graft polymeric moieties per polymer backbone chain on average, and wherein said water-soluble tackifying agent and said base polymer components are present in a weight ratio of from about 0.05:1 to about 1.5:1, respectively.

2. The pressure-sensitive adhesive of claim 1 wherein said tackifying agent is selected from the group consisting of polysorbitol, ethoxylated alkyl phenols, glycerol, polypropylene glycol and polyethylene glycol.

3. The pressure-sensitive adhesive of claim 1 wherein said tackifying agent has a molecular weight in the range of from about 50 to 20,000.

4. The pressure-sensitive adhesive of claim 1 wherein said tackifier and said base polymer component are present in a weight ratio of from about 0.25:1 to about 0.75:1, respectively.

5. The pressure-sensitive adhesive of claim 1 wherein said graft is a polymerized monoalkenyl-substituted aromatic hydrocarbon.

6. The pressure-sensitive adhesive of claim 2 wherein said polymerized monoalkenyl-substituted aromatic hydrocarbon comprises polystyrene.

7. The pressure-sensitive adhesive of claim 1 wherein the molecular weight of said graft is in the range of from about 30,000 to 60,000.

8. The pressure-sensitive adhesive of claim 1 wherein said graft is present in an amount of about 2 polymeric moieties per polymeric backbone chain on average.

9. The pressure-sensitive adhesive of claim 1 wherein said B monomer is selected from the group consisting of acrylic acid, methacrylic acid, itaconic acid, acrylamide, methacrylamide, acrylonitrile, methacrylonitrile, diacetone acrylamide, and 2-carboxyl ethyl esters of acrylic acid.

10. The pressure-sensitive adhesive of claim 1 comprising from about 50 to 80 percent by weight of said A monomer.

11. The pressure-sensitive adhesive of claim 10 comprising from about 50 to 65 percent by weight of said A monomer.

12. The pressure-sensitive adhesive of claim 1 wherein said A monomer comprises an ester of acrylic and methacrylic acid with a non-tertiary alcohol selected from the group consisting of 1-butanol, 1-pentanol, 2-pentanol, 3-pentanol, 2-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, and 1-docenanol.

13. The pressure-sensitive adhesive of claim 1 wherein said graft comprises poly-alpha-methylstyrene.

14. In combination, (1) a water-inactivatable pressure sensitive adhesive comprised of a hydrophilic/hydrophobic base polymer component in admixture with a water-soluble tackifying agent for said base polymer, said base polymer component comprising a phase separated graft copolymer composition comprised of copolymerized monomers A and B to form a backbone polymer having a polymeric moiety grafted thereto, wherein monomer A is a monomeric acrylic or methacrylic acid ester of a non-tertiary alcohol having from 1 to 14 carbon atoms, with the average number of carbon atoms being in the range of about 4 to 12, and monomer B is a polar monomer which is copolymerizable with monomer A, wherein said graft polymeric moiety is present in an amount of from about 1.5 to 2.5 graft polymeric moieties per polymer backbone chain on average, and wherein said water-soluble tackifying agent and said base polymer component are present in a weight ratio of from 0.05:1 to about 1.5:1, respectively, and (2) a water-absorbing backing support material to which said adhesive is applied.

15. The combination of claim 14, wherein said tackifying agent is selected from the group consisting of polysorbitol, ethoxylated alkyl phenols, glycerol, polypropylene glycol and polyethylene glycol.

16. The combination of claim 14, wherein said tackifying agent has a molecular weight in the range of from about 50 to 20,000.

17. The combination of claim 14, wherein said tackifier and said base polymer component are present in a weight ratio of from about 0.25:1 to about 0.75:1, respectively.

18. The combination of claim 14 wherein said graft is a polymerized monoalkenyl-substituted aromatic hydrocarbon.

19. The combination of claim 15 wherein said polymerized monoalkenyl-substituted aromatic hydrocarbon comprises polystyrene.

20. The combination of claim 14 wherein the molecular weight of said graft is in the range of from about 30,000 to 60,000.

21. The combination of claim 14 wherein said graft is present in an amount of about 2 polymeric moieties per polymeric backbone chain on average.

22. The combination of claim 14 wherein said B monomer is selected from the group consisting of acrylic acid, methacrylic acid, itaconic acid, acrylamide, methyacrylamide, acrylonitrile, methacrylonitrile, diacetone acrylamide, and 2-carboxy ethyl esters of acrylic acid.

23. The combination of claim 14 comprising from about 50 to 80 percent by weight of said A monomer.

24. The combination of claim 23 comprising from about 50 to 65 percent by weight of said A monomer.

25. The combination of claim 14 wherein said A monomer comprises an ester of acrylic and methacrylic acid with a non-tertiary alcohol selected from the group consisting of 1-butanol, 1-pentanol, 2-pentanol, 3-pentanol, 2-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, and 1-docenanol.

26. The combination of claim 14 wherein said graft comprises poly-alpha-methylstyrene.

* * * * *